(12) United States Patent
Pack

(10) Patent No.: US 7,933,375 B2
(45) Date of Patent: Apr. 26, 2011

(54) RAY CONSISTENCY BASED RECONSTRUCTION OF HELICAL CONE BEAM DATA

(75) Inventor: Jed Douglas Pack, Glenville, NY (US)

(73) Assignee: Morpho Detection, Inc., Newark, CA (US)

( * ) Notice: Subject to any disclaimer, the term of this patent is extended or adjusted under 35 U.S.C. 154(b) by 761 days.

(21) Appl. No.: 11/771,297

(22) Filed: Jun. 29, 2007

(65) Prior Publication Data

US 2008/0192886 A1    Aug. 14, 2008

Related U.S. Application Data

(60) Provisional application No. 60/845,593, filed on Sep. 19, 2006.

(51) Int. Cl.
*A61B 6/03* (2006.01)
(52) U.S. Cl. .......................... 378/4; 378/901
(58) Field of Classification Search ............... 378/4, 15, 378/901
See application file for complete search history.

(56) References Cited

U.S. PATENT DOCUMENTS

| | | | |
|---|---|---|---|
| 5,802,134 A | 9/1998 | Larson et al. | |
| 6,343,108 B1 * | 1/2002 | Heuscher | 378/4 |
| 6,529,575 B1 * | 3/2003 | Hsieh | 378/4 |
| 6,574,298 B2 * | 6/2003 | Heuscher | 378/15 |
| 2005/0123092 A1 * | 6/2005 | Mistretta et al. | 378/23 |
| 2006/0067458 A1 * | 3/2006 | Chen | 378/4 |

FOREIGN PATENT DOCUMENTS

WO    WO2004111945 A2    12/2004

OTHER PUBLICATIONS

Class Definition for Class 378, X-ray or Gamma Ray Systems or Devices, USPTO Class Definitions.*
Chen, Cone-Beam Multi-Slice Spiral Computed Tomography: Novel Reconstruction and Applications, 2002, Ph.D. Thesis, Purdue University, 136 pages including cover pages.*
Heuscher et al., Helical Cone Beam Scans Using Oblique 2D Surface Reconstruction, 1999, Proceedings of the 1999 International Meeting on Fully Three-dimensional Image Reconstruction in Radiology and Nuclear Medicine, pp. 204-207.*

(Continued)

*Primary Examiner* — Edward J Glick
*Assistant Examiner* — John M Corbett
(74) *Attorney, Agent, or Firm* — Armstrong Teasdale LLP

(57) ABSTRACT

A CT imaging system includes a computer that is programmed to rebin cone beam projection data into a series of two-dimensional sinograms based on an optimized ray consistency approach. The computer receives cone beam data from a detector array and is programmed to specify a plurality of view angles for the cone beam data. The computer selects a plurality of measured rays for each of the plurality of specified view angles, the plurality of measured rays having a view angle approximate to the specified view angle as determined by an optimized ray consistency. The computer also forms a two-dimensional sinogram for each of the plurality of specified view angles based on the selected plurality of measured rays. The computer then defines an image surface for each of the plurality of specified view angles based on the selected plurality of measured rays.

29 Claims, 6 Drawing Sheets

OTHER PUBLICATIONS

Tang et al., A three-dimensional weighted cone beam filtered backprojection (CB-FBP) algorithm for image reconstruction in volume CT under a circular source trajectory, Aug. 3, 2005, Physics in Medicine and Biology, vol. 50, pp. 3889-3905.*

Hsieh, Computed Tomography: Principles, Designs, Artifacts and Recent Advances, 2003, SPIE Press, ISBN 0-8194-4425-1, pp. 168-183 and 212.*

S.K. Patch, "Consistency conditions upon 3D CT data and the wave equation", Institute of Physics Publishing, Physics in Medicine and Biology, Phys. Med. Biol. 47, pp. 2637-2650, 2002.

Michel Defrise, Frederic Noo, and Hiroyuki Kudo, "Improved two-dimensional rebinning of helical cone-beam computerized tomography data using John's equation". Institute of Physics Publishing, Inverse Problems, Inverse Problems 19, pp. S41-S54, 2003.

PCT International Search Report dated Apr. 1, 2008, PCT/US2007/074273, 6 pages.

Patch, "Consistency Conditions Upon 3D CT Data and the Wave Equation", Physics in Medicine and Biology, vol. 47, No. 15, pp. 5637-2650, Aug. 7, 2002.

Defrise et al., "Improved Two-Dimensional Rebinning of Helical Cone-Beam Computerized Tomography Data Using John's Equation", Inverse Problems, vol. 19, No. 6, pp. S41-S54, Dec. 2003.

Michel Defrise, Frederic Noo, and Hiroyuki Kudo, "Rebinning-based algorithms for helical cone-beam CT", Institute of Physics Publishing, Physics in Medicine and Biology, Phys. Med. Biol. 46, pp. 2911-2937, 2001.

* cited by examiner

RAY CONSISTENCY BASED RECONSTRUCTION OF HELICAL CONE BEAM DATA

CROSS-REFERENCE TO RELATED APPLICATION

The present application is a non-provisional of, and claims priority to, provisional U.S. patent application No. 60/845,593 filed Sep. 19, 2006.

BACKGROUND OF THE INVENTION

The present invention relates generally to the field of image reconstruction in computed tomography (CT) systems and, more particularly, to a method and apparatus for rebinning cone beam projection data into a series of two-dimensional sinograms based on an optimized ray consistency approach.

Computed tomography (CT) imaging systems operate by projecting fan shaped or cone shaped X-ray beams through an object. The X-ray beams are generated by an X-ray source, and are generally collimated prior to passing through the object being scanned. The attenuated beams are then detected by a set of detector elements. The detector elements produce a signal based on the intensity of the attenuated X-ray beams, and the signals are processed to produce projections. By using reconstruction techniques, such as filtered backprojection, useful images are formed from these projections.

A computer is able to process and reconstruct images of the portions of the object responsible for the radiation attenuation. As will be appreciated by those skilled in the art, these images are computed by processing a series of angularly displaced projection images. This data is then reconstructed to produce the reconstructed image, which is typically displayed on a display monitor, and may then be printed or reproduced on film or further processed by other software, such as computer aided detection software. When performing a CT scan where a cone-beam of x-rays is projected toward an object, special challenges are introduced into image reconstruction. That is, 3D image reconstruction of cone-beam projections poses significant challenges in regards to reconstruction algorithms that accurately and efficiently produce a CT image. This holds true, in particular, for a helical scan geometry, where the x-ray source moves along a segment of a helix relative to the object.

Previously, several algorithms have been developed to reconstruct cone beam data. One such algorithm is the Feldkamp algorithm, which is an approximate reconstruction algorithm for helical cone beam CT. The Feldkamp algorithm is a 3D filtered backprojection (FBP) algorithm in which a 1D row-by-row filtering of each projection and cone beam backprojection is performed, using either a full-scan or a short-scan set of data to reconstruct transaxial slices. This cone beam backprojection leads to numerical inefficiency in the reconstruction of the FDK algorithm.

Another algorithm that has been developed to reconstruct cone beam data is the PHI algorithm. The PHI algorithm is an exact/quasi-exact algorithm that yields accurate reconstructions by discretizing exact analytical inversion formulae for a 3D divergent-beam x-ray transform. This exact or quasi-exact algorithm yields accurate reconstructions even for very large values of the cone-angle. However, it involves complex data processing compared to two-dimensional (2D) reconstruction approaches and this complexity increases the reconstruction time by more than one order of magnitude. Thus, while accurate, the PHI algorithm is slow and numerically complex.

In order to decrease reconstruction time for helical cone-beam CT over the above mentioned techniques, and other similar techniques, rebinning is often used to convert cone beam data into a series of approximate 2D sinograms. This allows for the reconstruction of a plurality of 2D sinograms, which is less computationally intensive than 3D reconstruction, and is thus much more efficient. One drawback to current rebinning methods, however, is that most of the rays needed in the 2D sinograms are not actually measured. Rather, the majority of the rays used in the sinograms are approximated using the available data received from the cone beam. This approximation introduces errors that can result in significant errors in the final reconstructed image.

In the case of reconstructing data obtained in a helical cone-beam CT scan by way of 2D reconstruction algorithms, a set of 2D sinograms is generated from the cone beam data. If 2D parallel beam reconstruction is used, cone beam data is rebinned from a cone beam to a cone-parallel geometry. After this rebinning, the data is described by the function $g(\beta,s,\gamma)$, where $\beta$ is the (parallel) view angle, s denotes the signed distance between the rotation axis and the ray, and $\gamma$ is the cone angle of the ray. Note that the variable $\beta$ increases by $2\pi$ for each rotation of the helix—it does not, for example, wrap back around to zero after each rotation. This data can be rebinned to 2D parallel data at a series of z locations $(z_n)$ as follows:

$$p(\theta,s,z_n) = w_r(\zeta_1,s)g(\beta_n+\zeta_1,s,\gamma(\zeta_1,s)) + w_r(\zeta_2,-s)g(\beta_n+\zeta_2,-s,\gamma(\zeta_2,-s)) \quad \text{[Eqn. A]},$$

with $\zeta_1 = \mod(\theta-\beta_n+\pi, 2\pi)-\pi$ and $\zeta_2 = \mod(\theta-\beta_n, 2\pi)-\pi$, and $\beta_n$ being the parallel view angle associated with $z_n$, and where $\gamma(\zeta,s)$ is a cone angle that covers a domain of $\zeta$ from $-\pi$ to $\pi$ and s, from $-R_o$ to $R_o$, where $R_o$ is the radius of the field of view, and where $w_r(\zeta,s)$ is a redundancy weight that covers the same domain and has the property that $w_r(\zeta,s)+w_r(\zeta+\pi,-s)=1$ when $\zeta<0$. Also, $p(\theta,s,z)$ is computed over a domain of $\theta$ from 0 to $\pi$ and s from $-R_o$ to $R_o$.

In one previously known technique, $w_r(\zeta,s)=1$ for $|\zeta|<\pi/2$. This implies $w_r$ is equal to zero elsewhere. Additionally, for the function $\gamma$, the value of the function is set such that:

$$\tan(\gamma) = (z_n-z_s)/(2*\sqrt{R^2-s^2}) \quad \text{[Eqn. B]},$$

where $z_s$ is the z location of the source when the rays $g(\beta_n+\zeta,s)$ are measured. This choice of the function $\gamma$ corresponds to a traditional helical interpolation and leads to an approximation of the 2D sinogram for an axial slice of an image volume. While computationally more efficient than 3D reconstruction algorithms, a drawback to this technique is that the approximation error present in approximating the 2D sinograms is very high. As such, a loss of resolution occurs in the final reconstructed image.

In another known technique set forth in U.S. Pat. No. 5,802,134 to Larson et al., planar axial slices (i.e., image slices) in the imaging volume are defined such that they define a tilt angle and a rotation angle with respect to a rotation axis (i.e., the z axis or longitudinal axis). Successive planar slices have equal tilt angles but changing rotation angles such that normal axes of successive slices define a nutation and precession about the rotation axis. That is, the function $\gamma(\zeta,s)$ is chosen such that rays in the cone beam are as consistent as possible with the pre-selected planar slice. Thus, by attempting to select rays most consistent with a pre-defined plane, a plurality of the rays used in reconstructing the 2D sinograms for the planar image slices are still approximated, which can lead to errors in the final reconstructed image.

Therefore, it would be desirable to design an improved apparatus and method that generates a plurality of 2D sinograms to reduce the reconstruction time for helical cone beam data. It is also desirable to design an apparatus and method for rebinning cone beam data that reduces the error associated with the rebinning process.

BRIEF DESCRIPTION OF THE INVENTION

The present invention is a directed method and apparatus for rebinning cone beam projection data into a series of two-dimensional sinograms based on an optimized ray consistency approach.

According to one aspect of the present invention, a CT imaging system includes a rotatable gantry having an opening to receive an object to be scanned, a high frequency electromagnetic energy projection source configured to project a cone beam of high frequency electromagnetic rays toward the object, and a detector array to detect the cone beam of high frequency electromagnetic rays and generate cone beam data therefrom. The CT imaging system also includes a computer, the computer being programmed to: receive the cone beam data from the detector array, specify a plurality of view angles, and select a plurality of measured rays for each of the plurality of specified view angles, the plurality of measured rays having a view angle approximate to the specified view angle as determined by an optimized ray consistency. The computer is also programmed to form a two-dimensional sinogram for each of the plurality of specified view angles based on the selected plurality of measured rays and define an image surface for each of the plurality of specified view angles based on the selected plurality of measured rays.

According to another aspect of the present invention, a computer readable storage medium includes a computer program stored thereon representing a set of instructions, that when executed by a computer, causes the computer to acquire projection data from a cone beam of x-rays detected by a detector array, the cone beam projection data acquired for an imaging volume, and re-bin the cone beam projection data to parallel geometry cone data, wherein x-rays in the parallel geometry cone data are defined as a function of a cone angle, in-plane displacement relative to a rotation axis, and a view angle. The instructions further cause the computer to select x-rays from the parallel geometry cone data having a cone angle and redundancy weight that minimize an inconsistency between the x-rays, determine a plurality of image surfaces from the selected x-rays, and form a two-dimensional sinogram for each of the plurality of image surfaces.

According to yet another aspect of the present invention, a method of image reconstruction of cone beam CT data includes the steps of receiving x-ray cone beam data in a helix pattern for a plurality of points along a longitudinal axis and specifying a plurality of view angles about the longitudinal axis at which to form two-dimensional sinograms. For each of the plurality of specified view angles, the method further includes the steps of selecting a plurality of x-rays from the cone beam data having a view angle in proximity to the specified view angle based on an optimized ray consistency between x-rays in the cone beam data, generating the two-dimensional sinogram from the selected plurality of x-rays, and associating a two-dimensional image surface with the sinogram the two-dimensional surface having a best fit with the selected plurality of x-rays.

Various other features and advantages of the present invention will be made apparent from the following detailed description and the drawings.

BRIEF DESCRIPTION OF THE DRAWINGS

The drawings illustrate one preferred embodiment presently contemplated for carrying out the invention.

In the drawings.

DETAILED DESCRIPTION OF THE PREFERRED EMBODIMENT

The operating environment of the present invention is described with respect to a sixty-four-slice computed tomography (CT) system. However, it will be appreciated by those skilled in the art that the present invention is equally applicable for use with other multi-slice configurations. Moreover, the present invention will be described with respect to the detection and conversion of x-rays. However, one skilled in the art will further appreciate that the present invention is equally applicable for the detection and conversion of other high frequency electromagnetic energy. The present invention will be described with respect to a "third generation" CT scanner, but is equally applicable with other CT systems.

Figure 1:
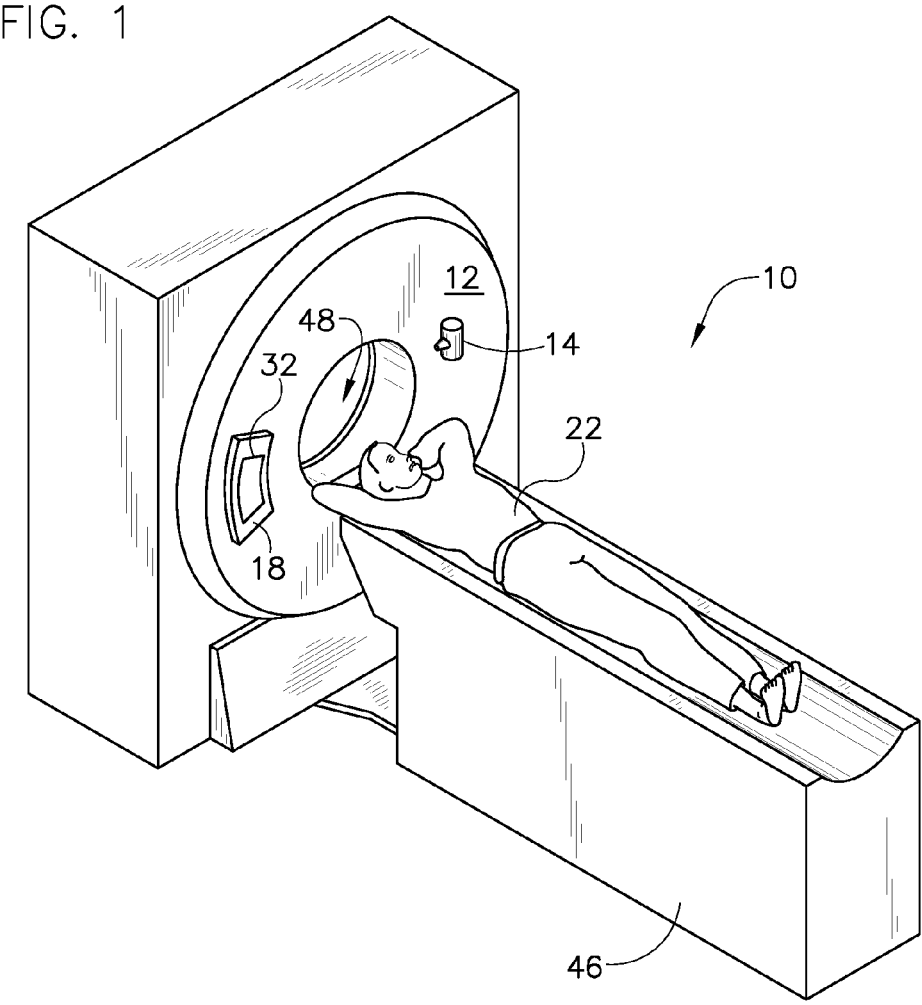
FIG. 1 is a pictorial view of a CT imaging system.
Figure 2:
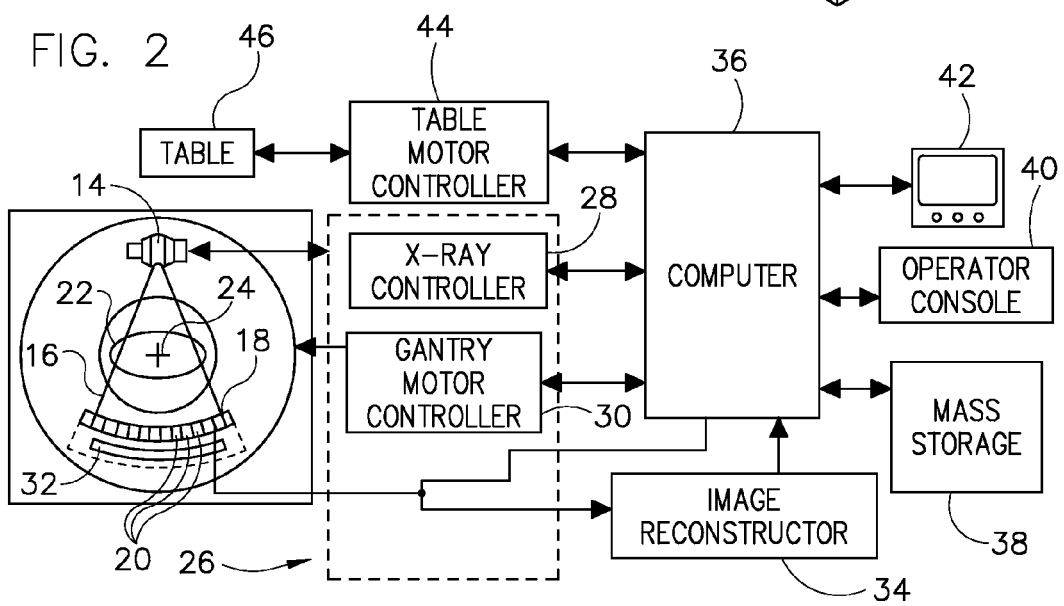
FIG. 2 is a block schematic diagram of the system illustrated in FIG. 1.

Referring to FIG. 1, a computed tomography (CT) imaging system 10 is shown as including a gantry 12 representative of a "third generation" CT scanner. Gantry 12 has an x-ray source 14 that projects a beam of x-rays 16 toward a detector assembly or collimator 18 on the opposite side of the gantry 12. Referring now to FIG. 2, detector assembly 18 is formed by a plurality of detectors 20 and data acquisition systems (DAS) 32. The plurality of detectors 20 sense the projected x-rays that pass through a medical patient 22, and DAS 32 converts the data to digital signals for subsequent processing. Each detector 20 produces an analog electrical signal that represents the intensity of an impinging x-ray beam and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has some form of operator interface, such as a keyboard, mouse, voice activated controller, or any other suitable input apparatus. An associated display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 12. Particularly, table 46 moves patients 22 through a gantry opening 48 of FIG. 1 in whole or in part.

Figure 3:
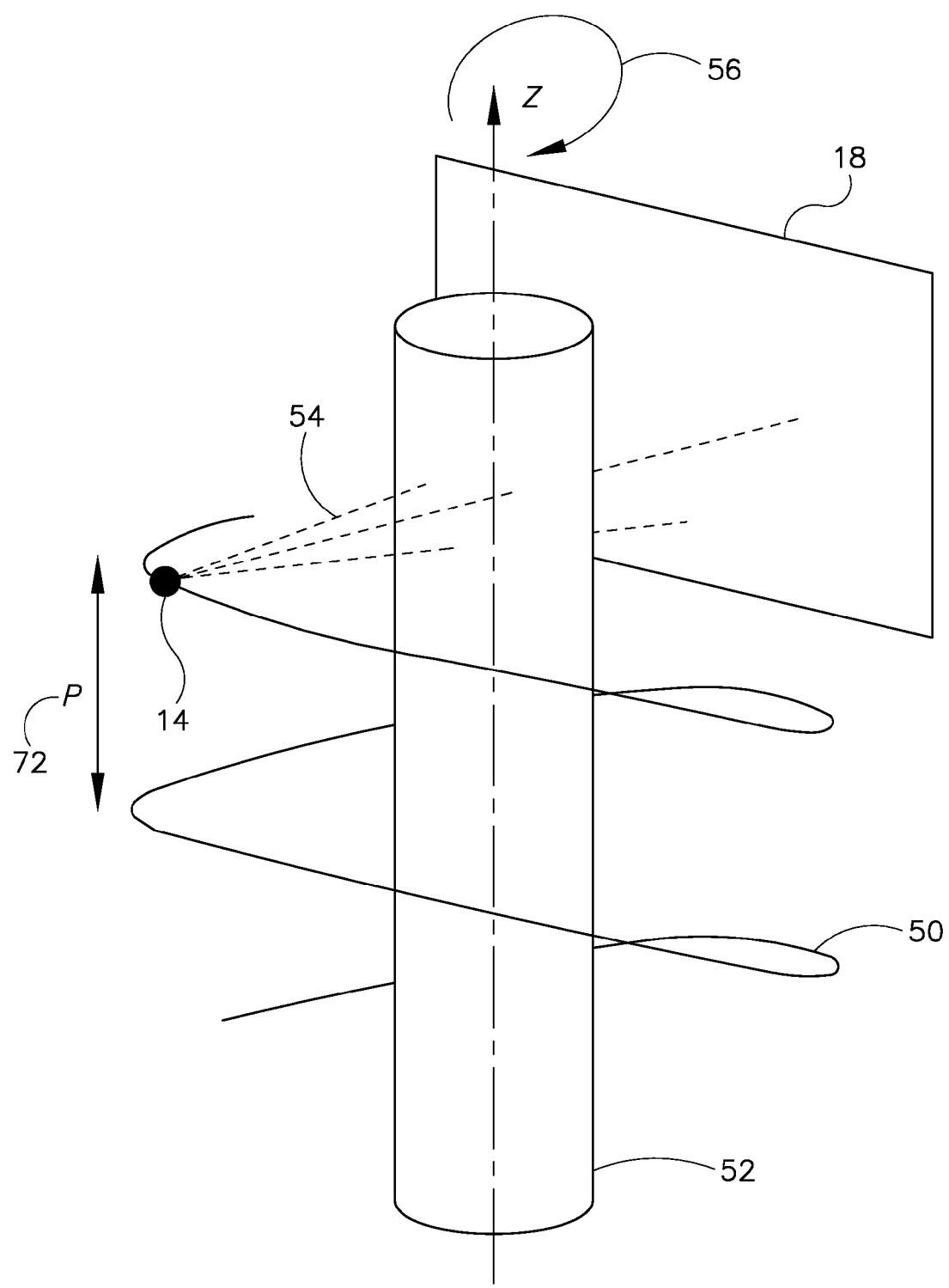
FIG. 3 is a graphical representation of a helical scanning path performed by the system illustrated in FIG. 1.

Referring now to FIG. 3, a helical or spiral scanning pattern 50 is shown according to one embodiment of the invention. In the helical scanning pattern, the object 52 being scanned is translated along the z-axis while the source 14 and detector array 18 are rotated about the object 52 and a cone beam of x-rays 54 are emitted toward the object 52. In helical scanning, the projection data acquired by detector array 18 is normally acquired such that z is linearly related to a view angle 56, $\beta$, so that $z(\beta)=c\beta$, where c is a constant. If the object 52 is continuously translated in the direction of the z-axis while the source 14 and detector 18 are rotated about the object 52, none of the scanning planes will be co-planar.

In order to reconstruct images from the projection data acquired during the helical CT scan, a rebinning algorithm is introduced. The goal of the rebinning algorithm is the formation of a plurality of two-dimensional sinograms from which a plurality of 2D images can be reconstructed. A significant factor in defining a rebinning algorithm is the choice of image surfaces for which the 2D sinograms will be estimated. For each image surface, each ray in the 2D sinogram is approximated by interpolating the measured cone beam data. Ideally, all measured rays used for this purpose should lie within the image surface; however, with a helical scan path 50 this condition cannot be satisfied and the rebinning algorithms are only approximate. To optimize the accuracy of a specific algorithm, the rays used for rebinning should be selected as close as possible to the image surface to reconstruct, and the extent to which this can be done depends on the choice of the surface.

While previously applied algorithms in the art have selected rays based on their relationship to a set of pre-defined image surfaces, the present invention does not pre-define any image surfaces. Rather, a ray-consistency based algorithm is implemented to form the image surfaces based on a measured consistency between measured rays. That is, each ray used in forming the 2D sinogram is chosen based on its consistency with other rays.

Rather than choosing pre-defined image surfaces at which 2D sinograms are generated, the ray-consistency based approach pre-selects only a plurality of specified view angles, $\beta_n$, n=[1, 2, . . . N], about which sinograms are to be generated. That is, although an image surface will eventually need to be specified for each of the specified view angles, $\beta_n$, the image surface is not pre-determined. Rather, the rays are chosen so as to be as consistent as possible with each other, and the image surface is then chosen so as to be consistent with the selected rays. In one preferred embodiment, the plurality of specified view angles are equally spaced along the helix, and the interval between the view angles are chosen based on the number of 2D reconstructions that can be performed in a desired time frame selected by an operator.

For each of the view angles, $\beta_n$, a 2D sinogram is generated that covers all angles from 0 to $\pi$. The rays that are used to generate this sinogram come from the view angle range $\beta_n-\pi<\beta<\beta_n+\pi$. The rays selected for generating the sinogram are selected based on a minimum inconsistency between the rays. This inconsistency is determined by way of a pair of functions, $\gamma(\zeta, s)$ and $w_r(\zeta, s)$ that define a cone angle (i.e., the angle of a ray relative to the x-y plane) and redundancy weight, respectively. These functions are the same as those defined in Eqn A. The cone angle and redundancy weight are functions of the view angle displacement $\zeta$ (where $\zeta=\beta-\beta_n$) and an in-plane displacement, s, relative to a rotation axis, which is the z-axis/longitudinal axis. The redundancy weight has the property such that:

$$w_r(\zeta,s)+w_r(\zeta+\pi,-s)=1 \quad [\text{Eqn. 1}],$$

when $\zeta<0$.

The functions $\gamma$ and $w_r$ are chosen such that they minimize the inconsistency among the rays they define. This inconsistency can be mathematically defined by:

$$\text{Inconsistency}=\Sigma_{m=1\ to\ M}\Sigma_{k=1\ to\ K}\Sigma_{j=1\ to\ K}[w_r(\zeta_k,S(\zeta_k,x_m,y_m))*(w_r(\zeta_j,S(\zeta_j,x_m,y_m))*(z(x_m,y_m,k)-z(x_m,y_m,j))^2] \quad [\text{Eqn. 2}],$$

or, more generally as:

$$\text{Inconsistency}=\Sigma_{m=1\ to\ M}\Sigma_{k=1\ to\ K}\Sigma_{j=1\ to\ K}[w_r(\zeta_k,S(\zeta_k,x_m,y_m))*w_r(\zeta_j,S(\zeta_j,x_m,y_m))*(z(x_m,y_m,k)-z(x_m,y_m,j))^2+\eta*w_r(\zeta_j,S(\zeta_j,x_m,y_m))*(w_r(\zeta_k,S(\zeta_k,x_m,y_m))*z(x_m,y_m,k)+w_r(\zeta_{k'},S(\zeta_{k'},x_m,y_m))*z(x_m,y_m,k')-z(x_m,y_m,j))^2] \quad [\text{Eqn. 3}].$$

As set forth in the above equation, k' is the index of the view that is conjugate to the one indexed by k, M is the number of pixels in the xy plane within the field of view, K is the number of view angles in the range $-\pi$ to $\pi$, S is a function that gives the distance between a point and the origin in the s direction, and z is a function that gives the z position at which the surface of rays selected by the function $\gamma$ (at the given view angle) intersects the line parallel to the z axis which contains the point (x,y,0). Eta, $\eta$, is a free parameter. If it is set to zero, the second expression, Eqn. 3, reduces to the first expression, Eqn. 2. $\eta$ can be set to a non-zero value in recognition of the fact that when the object being imaged is smooth, a weighted average of two intersecting line integrals gives a good estimate of the line integral on another line that passes through the intersection of the first two. In effect, when q is greater than zero, additional rays are included in the optimization. These additional rays are formed as a weighted average of each ray with its conjugate, wherein the weights used in the average are defined by the redundancy weight function. As $\eta$ is increased, more emphasis is placed on these additional rays in the inconsistency minimization procedure.

Figure 4A:
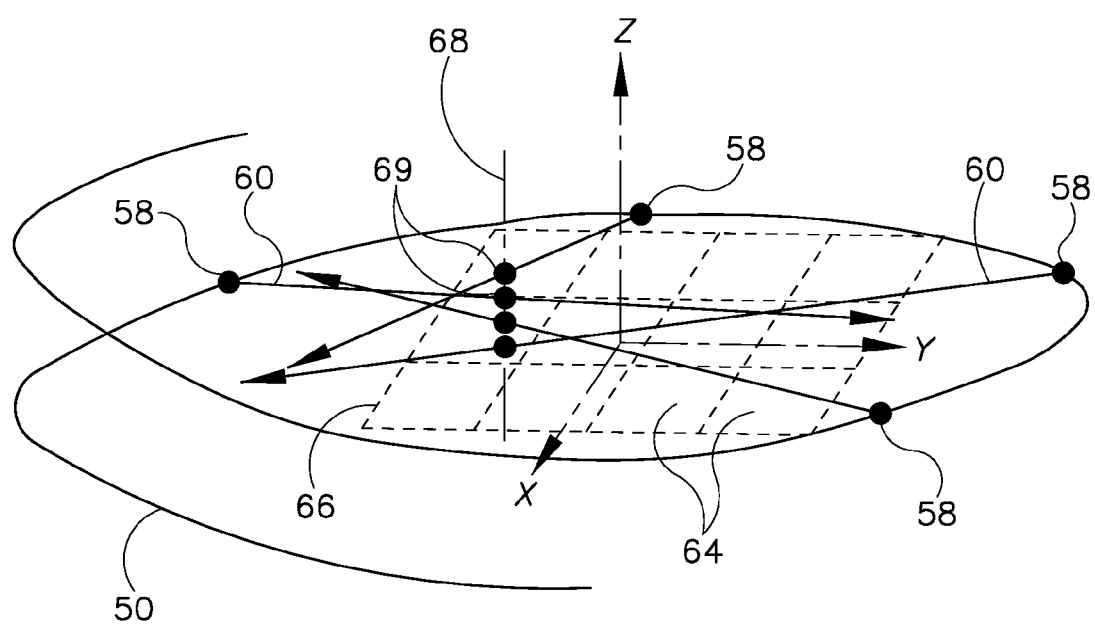
FIG. 4A is a perspective view of a schematic representation of the inconsistency between measured x-rays according to the present invention.
Figure 4B:
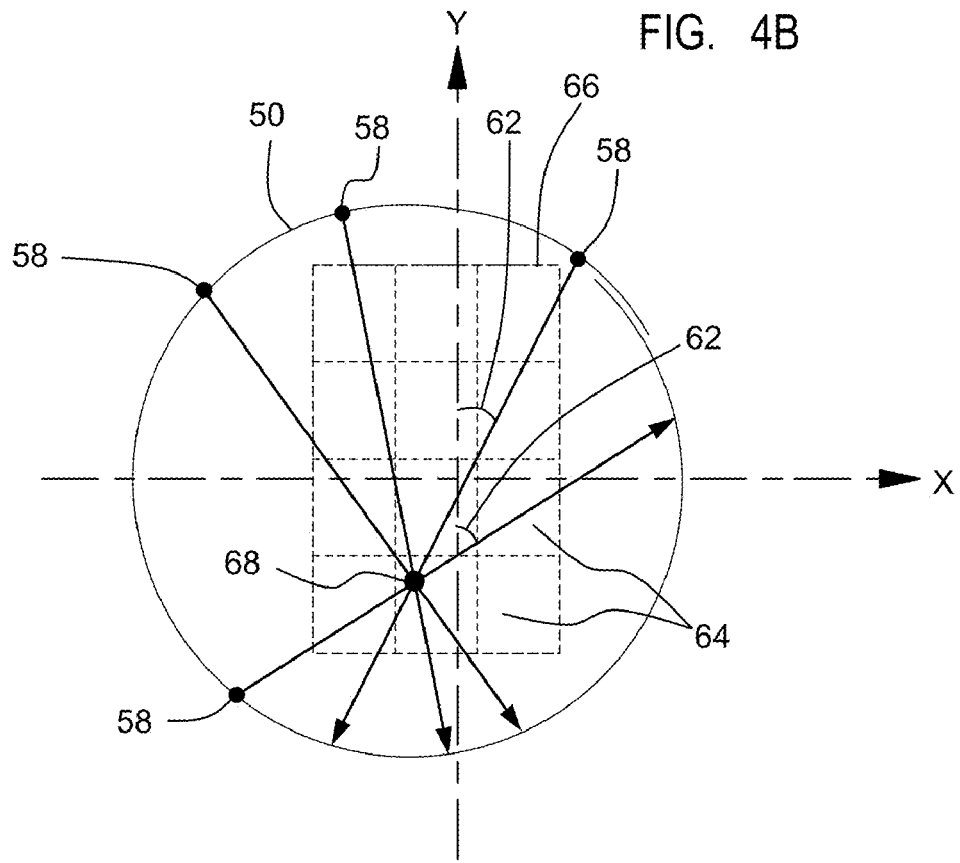
FIG. 4B is a top plan view of the schematic diagram of the inconsistency between measured x-rays illustrated in FIG. 4A.
Figure 4C:
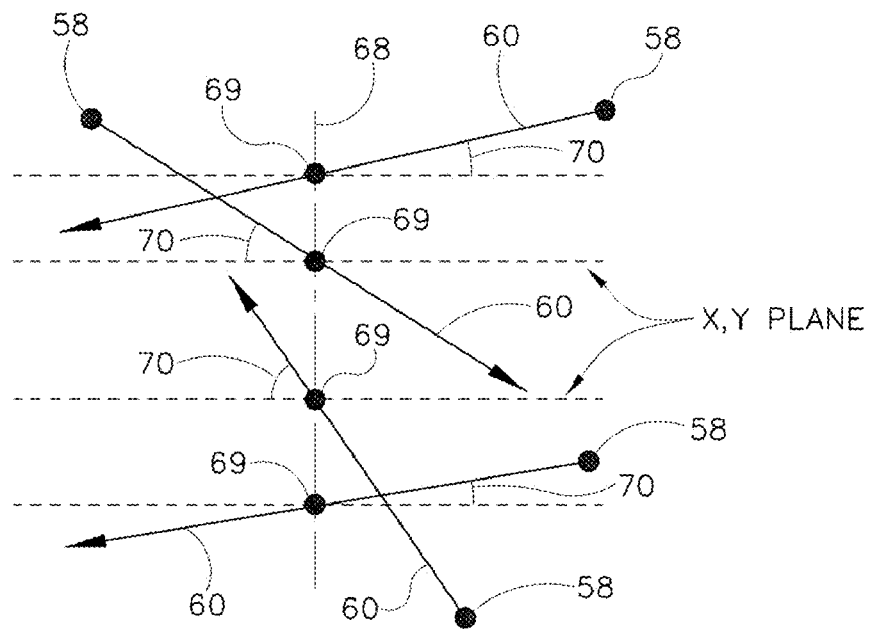
FIG. 4C is a side plan view of the schematic diagram of the inconsistency between measured x-rays illustrated in FIG. 4A.

FIGS. 4A-4C are a schematic representation of the inconsistency between measured rays in a portion of the helical scanning pattern 50 and show therein a number of source points 58 that are chosen along the helix. As shown in FIGS. 4A and 4B, each of the source points 58 corresponds to a measured ray 60 that is at, or close/approximate to one of the specified view angles 62. In the example provided, K=4 such that four view angles 62, $\beta$, are specified in the angular range, $\theta$, from $\beta_n-\pi$ to $\beta_n+\pi$. In a realistic scenario, K would likely be much higher (e.g., many hundreds), however, only the rays corresponding to four view angles are shown here for simplicity. For each pixel 64, m, in the xy plane within the field of view 66, a line 68 parallel to the z-axis is selected which passes through a point $(x_m, y_m, 0)$. Intersection points 69 are identified along the line 68 at the $x_m, y_m$ location at differing z values, as determined by the z value at which each of the four measured rays 60 passes through line 68. These intersection points are defined by a $(x_m, y_m, z(x_m, y_m, k))$ location for each of the four view angles 62 corresponding to values of k.

As set forth above, K number of measured rays 60 pass through a single (x,y) image location, one for each view angle. As shown in FIG. 4C, each of the measured rays 60 passes through line 68 at the selected (x,y) image location at an angle relative to the x-y plane. That is, each ray 60 has a defined cone angle 70 at which it passes through line 68. The functions γ and $w_r$ (for the cone angle and redundancy weight, respectively) are chosen such that the rays 60 have cone angles 70 that will minimize the distance in the z direction at which the rays intersect line 68, thus minimizing the inconsistency among the rays they define. Clearly, if the cone angles are chosen appropriately, all four rays will intersect the line 68 at the same location. However, each of the rays also intersects other lines that are parallel to 68 and the consistency of the rays that intersect all such lines must be considered. In other words, while FIGS. 4A-4C shown only a single line 68 at one of the pixels 64 in the field of view, additional lines 68 would be positioned at each of the other pixels 64 in the field of view 66 and the inconsistency of measured rays 60 passing through each of these lines would be measured as has been described above. The inconsistency at all locations would then be accumulated.

The minimization of the inconsistency functional can be accomplished through an iterative gradient descent method. In one embodiment, the iterative gradient descent algorithm is begun by setting the cone angle function and the redundancy weight function to initial values (i.e., $\gamma = \gamma^{(1)}$ and $r_w = r_w^{(1)}$). For example, the cone angle function could be set to zero everywhere and the redundancy weight could be set to 0.5 everywhere (Step A). A loop is then initiated in which a first inconsistency is calculated based on γ and $r_w$ (Step B). The gradient (G1) of the inconsistency functional is computed with respect to each element of γ (Step C). A second inconsistency is then calculated based on γ' and $r_w$, where γ' is derived from G1, γ, and a first step size parameter (Step D). The first inconsistency is then compared to the second inconsistency, and the smaller of the two is selected. If the second inconsistency is selected, γ is replaced with γ' (Step E). Otherwise, the first step size parameter is reduced.

Next, a gradient (G2) of the inconsistency functional with respect to $r_w$ is computed (Step F). A third inconsistency is then calculated based on γ and $r_w'$, where $r_w'$ is derived from G2, $r_w$, and a second step size parameter (Step G). The inconsistency selected in Step E is then compared to the third inconsistency, and the smaller of the two is selected (Step H). If the third inconsistency is selected, $r_w$ is replaced by $r_w'$, otherwise, the second step size parameter is reduced. Step B thru Step G are repeated until a stopping criterion is met. This criterion can, for example, be based on number of iterations or on a measure of the step size parameters.

This minimization of the inconsistency is performed only once and the results may be stored in a lookup table for use during reconstruction of the 2D sinograms that are generated at each of the specified view angles, $\beta_n$. That is, the optimization can be pre-computed, as it need not be repeated for each scan, or even for each scanner as long as the geometry is constant. In order to allow a speedy convergence, the following constraint, which is a result of the symmetry of the helix, may be incorporated into the iterative gradient descent algorithm:

$$\gamma(\zeta,s) = -\gamma(-\zeta,-s) \quad \text{[Eqn. 4]}.$$

It is also useful to note that constraints may be placed upon γ based on the size of the detector array, such as for example, $|\gamma| < \gamma_{max}$. Using such a constraint ensures that even if the pitch 72 (i.e., the speed at which the helical scanning is performed as a function of z-axis translation and rotation of the x-ray source about the z-axis, as shown in FIG. 3) is too high to capture the most consistent rays, the iterative gradient descent method set forth above will still yield an optimal set of functions (γ and $r_w$) for the geometry being studied.

Referring again to FIG. 4A, the gradient descent algorithm functions to minimize the separation in the z direction of the intersection points 69 along line 68 created by measured rays 60. Each of these measured rays 60 is attracted to each of the other rays. The attraction force is proportional to the separation in z, and the net force on any particular ray 60 from this (x,y) location will be oriented toward the average z location of all the rays. If this force is added to the forces acting on this ray from other image locations, $(x_m, y_m)$, the result is the derivative of the inconsistency with respect to the cone angle 70 of that measured ray 60. This can be implemented in a structure similar to a forward projection.

By the above process in which an optimized consistency is determined between measured rays, rays are selected to form or generate a 2D sinogram at each of the plurality of specified view angles, $\beta_n$. The formation of these sinograms is described by Eqn. A. Equation A makes use of the symmetry of the helix such that it can be used in the formation of each sinogram at each of the plurality of view angles. That is, the functions γ and $r_w$ are independent of the specified view angle, $\beta_n$.

For each view angle about which a 2D sinogram is formed, a 2D reconstruction technique can be implemented to reconstruct an image from the sinogram. For example, a direct Fourier method or 2D filtered backprojection (FBP) can be used to reconstruct a good estimate of an image for the surface at the specified view angle.

Figure 5:
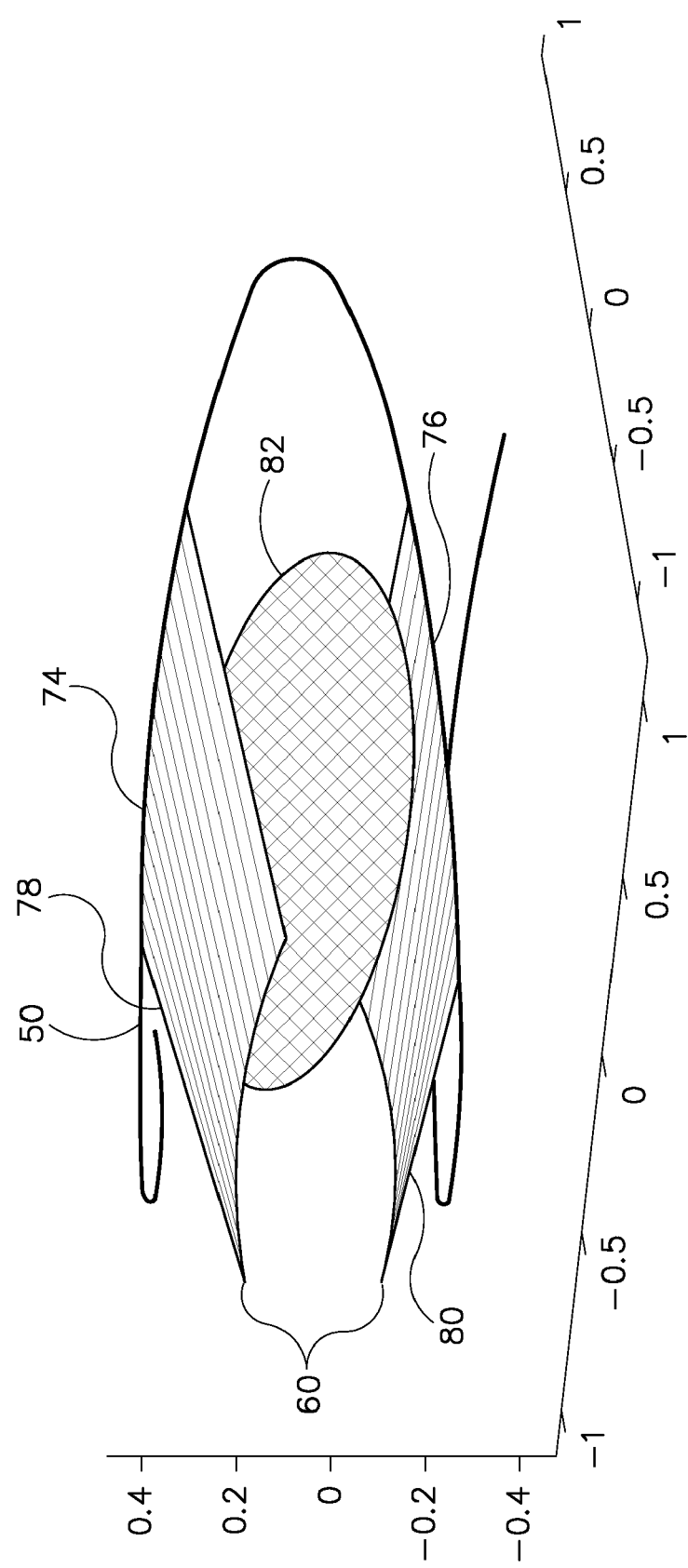
FIG. 5 is a schematic diagram of an image surface formed by measured x-rays at specified view angles along the helical scanning path according to the present invention.

For each of the N view angles specified about which rays have been selected to form a 2D sinogram, the location of the measured rays 60 can be examined to determine a 2D surface that is most consistent with (i.e., a best fit) the location of these rays. For example, FIG. 5 shows a portion of the helix 50 formed by the helical scanning pattern having measured rays 60 at two separate view angles 74, 76 where 2D sinograms are formed. A first set of rays 78 that are parallel to the xz plane are shown at the first view angle 74, and a second set of rays 80 that are parallel to the yz plane at the second view angle 76 are shown, the measured rays 60 intersecting the helix 50 as shown. As set forth above, the cone angle for each measured ray 60 is based on an optimized ray consistency that is a function of the inconsistency between the measured rays 60 as determined by γ and $w_r$. The set of rays 78, 80 at each of the specified view angles 74, 76 reflect a minimized inconsistency between measured rays 60 as determined by the selected cone angle for each measured ray 60 and are formed by the measured rays 60 to have a shape representative of the cone angles for each of the measured rays 60.

As shown in FIG. 5, an image surface 82 is determined by examining the location of first set of rays 78 and the location of second set of rays 80. Image surface 82 forms a 2D surface that is most consistent with (i.e., a best fit to) the location of the first and second sets of rays 78, 80 (and between all sets of rays for the number of specified view angles, $\beta_n$, n=[1, 2, . . . N]). This image surface will typically not be planar, but rather, will be a warped surface that is very consistent with a portion of the helix 50. That is, image surface 82 mimics the helix scanning pattern and will often have a warped surface, as the image surface is determined based on its relationship to measured rays 60 that each have varying cone angles relative to one another. Again, due to symmetry, each image surface 82 that is formed at a specified view angle will be identical to other image surfaces except for a rotation and a translation. Consequently, these additional image surfaces can also be easily pre-computed.

Each image surface 82 that is defined will thus form a two-dimensional image for each of the reconstructed sinograms. The two-dimensional images are comprised of a plurality of voxels on the respective image surfaces. The location of each of the plurality of voxels within a three-dimensional (3D) reconstruction cylinder is then determined to allow for reconstruction of a 3D image from the plurality of image surfaces, and the voxels thereon, that have been determined. In order to reconstruct such a 3D image, the plurality of voxels from each of the image surfaces is interpolated in the z-direction onto a rectilinear grid to form an image thereon. This interpolation step is optional, but if it is not done, a weighting function would need to be applied to the final image if it is to be used to compute the total x-ray mass or the total volume of a selected region. It should also be recognized that without this interpolation of the image in the z-direction, the images will exhibit a geometric distortion.

Figure 6:
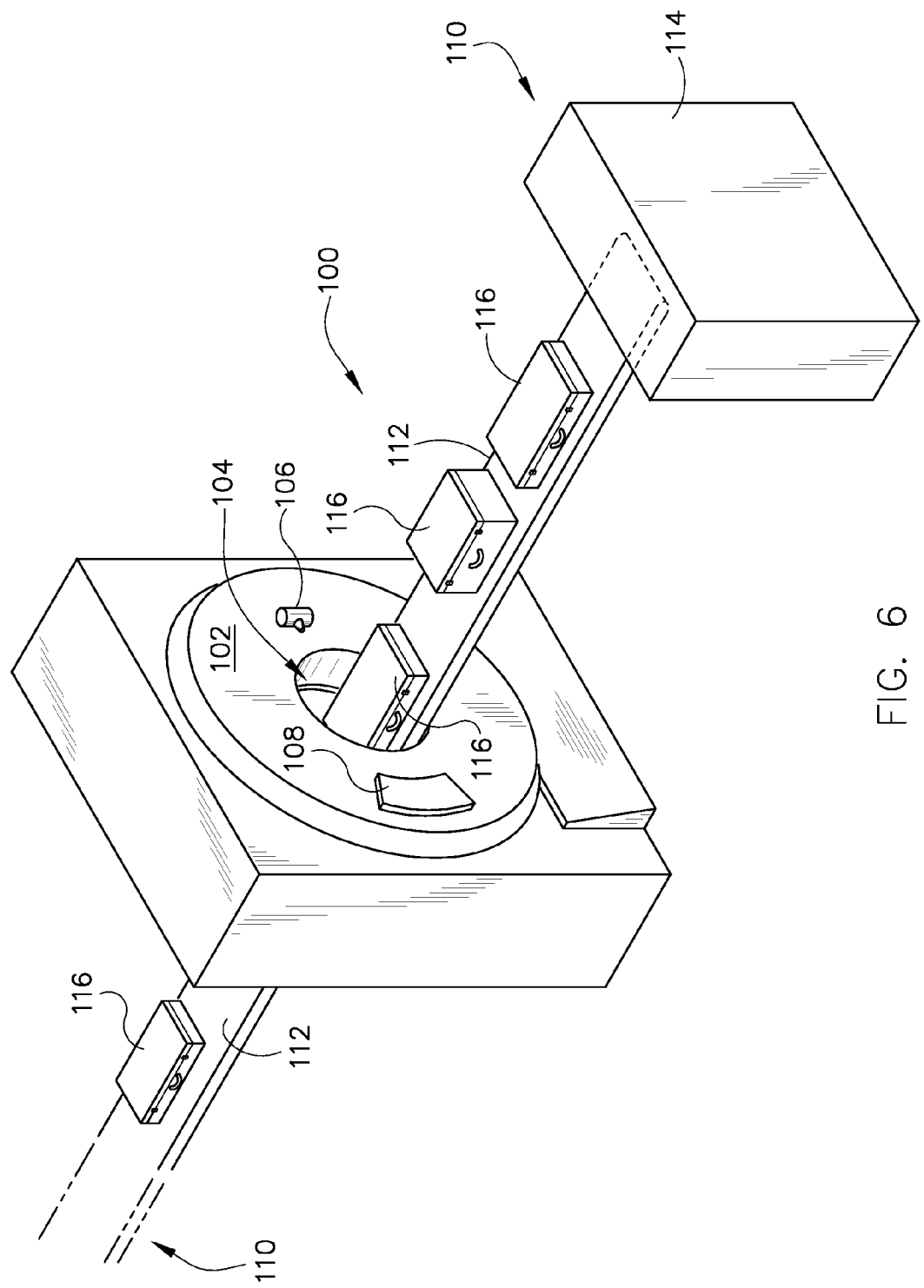
FIG. 6 is a pictorial view of a CT system for use with a non-invasive package inspection system.

Referring now to FIG. 6, it is envisioned that a package/baggage inspection system 100 can incorporate a ray-consistency based reconstruction technique in reconstructing images of baggage scanned therein. Package/baggage inspection system 100 includes a rotatable gantry 102 having an opening 104 therein through which packages or pieces of baggage may pass. The rotatable gantry 102 houses a high frequency electromagnetic energy source 106 that emits a cone beam of rays as well as a detector assembly 108 having scintillator arrays comprised of scintillator cells. A conveyor system 110 is also provided and includes a conveyor belt 112 supported by structure 114 to automatically and continuously pass packages or baggage pieces 116 through opening 104 to be scanned. Objects 116 are fed through opening 104 by conveyor belt 112 and imaging data is then acquired, the imaging data corresponding to a helical scan pattern of cone beam data, as the high frequency electromagnetic energy source 106 and the detector assembly 108 rotate about the continuously moving conveyor belt 112 and baggage pieces 116. This helical pattern of cone beam data is then reconstructed in system 100 by way of the ray-consistency based reconstruction technique set forth in detail above to reconstruct images of baggage 116. The conveyor belt 112 also functions to remove the packages 116 from opening 104 in a controlled and continuous manner after scanning is completed. As a result, postal inspectors, baggage handlers, and other security personnel may non-invasively inspect the contents of packages 116 for explosives, knives, guns, contraband, etc.

While the above technique has been described for use with a CT imaging process in which x-rays are emitted through an object of interest, it is also envisioned that other types of high frequency electromagnetic energy, such as gamma rays, could also be emitted and received in similar imaging processes. Furthermore, while a helical CT scanning pattern has been described above, it is also envisioned that ray-consistency based reconstruction could be implemented for a step-and-shoot CT system in which cone beam data is reconstructed.

A technical contribution for the disclosed method and apparatus is that is provides for a computer implemented technique for reconstruction in computed tomography (CT) systems. More particularly, the disclosed method and apparatus provides for rebinning cone beam projection data into a series of two-dimensional sinograms based on an optimized ray consistency approach.

Therefore, according to one embodiment of the present invention, a CT imaging system includes a rotatable gantry having an opening to receive an object to be scanned, a high frequency electromagnetic energy projection source configured to project a cone beam of high frequency electromagnetic rays toward the object, and a detector array to detect the cone beam of high frequency electromagnetic rays and generate cone beam data therefrom. The CT imaging system also includes a computer, the computer being programmed to: receive the cone beam data from the detector array, specify a plurality of view angles, and select a plurality of measured rays for each of the plurality of specified view angles, the plurality of measured rays having a view angle approximate to the specified view angle as determined by an optimized ray consistency. The computer is also programmed to form a two-dimensional sinogram for each of the plurality of specified view angles based on the selected plurality of measured rays and define an image surface for each of the plurality of specified view angles based on the selected plurality of measured rays.

According to another embodiment of the present invention, a computer readable storage medium includes a computer program stored thereon representing a set of instructions, that when executed by a computer, causes the computer to acquire projection data from a cone beam of x-rays detected by a detector array, the cone beam projection data acquired for an imaging volume, and re-bin the cone beam projection data to parallel geometry cone data, wherein x-rays in the parallel geometry cone data are defined as a function of a cone angle, in-plane displacement relative to a rotation axis, and a view angle. The instructions further cause the computer to select x-rays from the parallel geometry cone data having a cone angle and redundancy weight that minimize an inconsistency between the x-rays, determine a plurality of image surfaces from the selected x-rays, and form a two-dimensional sinogram for each of the plurality of image surfaces.

According to yet another embodiment of the present invention, a method of image reconstruction of cone beam CT data includes the steps of receiving x-ray cone beam data in a helix pattern for a plurality of points along a longitudinal axis and specifying a plurality of view angles about the longitudinal axis about which to form two-dimensional sinograms. For each of the plurality of specified view angles, the method further includes the steps of selecting a plurality of x-rays from the cone beam data having a view angle in proximity to the specified view angle based on an optimized ray consistency between x-rays in the cone beam data, generating the two-dimensional sinogram from the selected plurality of x-rays, and associating a two-dimensional image surface with the sinogram the two-dimensional surface having a best fit with the selected plurality of x-rays.

The present invention has been described in terms of the preferred embodiment, and it is recognized that equivalents, alternatives, and modifications, aside from those expressly stated, are possible and within the scope of the appending claims.

What is claimed is:

1. A computed tomography (CT) imaging system comprising:
   a rotatable gantry having an opening through which at least a portion of an object passes through during a scan;
   an energy source configured to project rays toward the object;
   a detector assembly configured to detect rays projected by the energy source that pass through the object and generate projection data therefrom; and
   a computer programmed to:
      receive the projection data from the detector assembly;
      for a selected view angle, identify measured rays consistent with each other;
      form a two-dimensional sinogram for the selected view angle based on the identified measured rays; and
      define an image surface for the selected view angle based on the identified measured rays.

2. The CT imaging system of claim 1 wherein to identify measured rays consistent with each other, the computer is further programmed to:
calculate an inconsistency among rays in the projection data; and
minimize the inconsistency among the rays.

3. The CT imaging system of claim 2 wherein the computer is further programmed to calculate the inconsistency by:

Inconsistency=$\Sigma_{m=1\ to\ M}\Sigma_{k=1\ to\ K}\Sigma_{j=1\ to\ K}\{w_r(\zeta_k,S(\zeta_k,x_m,y_m))*w_r(\zeta_j,S(\zeta_j,x_m,y_m))*(z(x_m,y_m,k)-z(x_m,y_m,j))^2+\eta*w_r(\zeta_j,S(\zeta_j,x_m,y_m))*(w_r(\zeta_k,S(\zeta_k,x_m,y_m))*z(x_m,y_m,k)+w_r(\zeta_{k'},S(\zeta_{k'},x_m,y_m))*z(x_m,y_m,k')-z(x_m,y_m,j))^2\}$ where $w_r$ is a redundancy weight, S is a function that gives a distance between a point and the origin in an s direction, $\zeta$ is a view angle displacement, $\eta$ relates to a number of rays used to calculate the inconsistency, and k' is an index of a view that is a conjugate to a view indexed by k.

4. The CT imaging system of claim 2 wherein the computer is further programmed to perform an iterative gradient descent algorithm to minimize the inconsistency.

5. The CT imaging system of claim 2, wherein the computer is further programmed to store inconsistency data in a memory area, and to form the two-dimensional sinogram for the selected view angle based on the stored consistency data to facilitate an enhanced response time.

6. The CT imaging system of claim 2, further comprising means for storing the minimized inconsistency among the rays in the projection data such that a subsequent formation of the two-dimensional sinogram for the selected view angle is based on the stored minimized inconsistency.

7. The CT imaging system of claim 1 wherein the computer is further programmed to perform a reconstruction on the two-dimensional sinogram for the selected view angle to obtain image data.

8. The CT imaging system of claim 7 wherein the computer is further programmed to perform one of a two-dimensional filtered backprojection (FBP) and a direct Fourier reconstruction on the two-dimensional sinogram.

9. The CT imaging system of claim 7 wherein the computer is further programmed to axially interpolate the image data from the image surface at the selected view angle to a rectilinear grid.

10. The CT imaging system of claim 1 wherein the computer is further programmed to form the two-dimensional sinogram at the selected view angle by:

$p(\theta,s,z_n)=w_r(\zeta_1,s)g(\beta_n+\zeta_1,s,\gamma(\zeta_1,s))+w_r(\zeta_2-\pi,-s)g(\beta_n+\zeta_2,-s,\gamma(\zeta_2,-s))$ where p is two-dimensional parallel data as a function of $\theta$, s, and $z_n$; $w_r$ is a redundancy weight as a function of $\zeta_1$ and s or $\zeta_2$ and s; g is rebinned beam data as a function of $\beta$, s, and $\gamma$; $\gamma$ is a cone angle of a ray; $\theta$ is an angle along a helix; s is a signed distance between a rotation axis of the helix and the ray having a cone angle of $\gamma$; $z_n$ is an $n^{th}$ location in a z-direction; $\zeta_1$ and $\zeta_2$ are functions of $\theta$ and $\beta_n$; and $\beta_n$ is a parallel view angle.

11. The CT imaging system of claim 1 wherein the computer is further programmed to receive cone beam data in a helix pattern about a longitudinal axis for a plurality of points along the longitudinal axis.

12. The CT imaging system of claim 11 wherein the computer is further programmed to equally space a plurality of view angles along the helix.

13. The CT imaging system of claim 12 wherein the computer is further programmed to specify the plurality of view angles based on a number of two-dimensional sinogram reconstructions that can be performed in a specified time frame.

14. The CT imaging system of claim 11 wherein the image surface is a non-planar surface that approximates the helix pattern.

15. A non-transitory computer readable storage medium having a computer program stored thereon and representing a set of instructions that when executed by a computer causes the computer to:
acquire projection data from a cone beam of x-rays detected by a detector assembly, the cone beam projection data acquired for an imaging volume;
re-bin the cone beam projection data to parallel geometry cone data, wherein x-rays in the parallel geometry cone data are defined as a function of a cone angle, in-plane displacement relative to a rotation axis, and a view angle;
for a selected view angle, identify measured x-rays consistent with each other;
form a two-dimensional sinogram for the selected view angle based on the identified measured x-rays consistent with each other; and
define an image surface for the selected view angle based on the identified measured x-rays.

16. The computer readable storage medium of claim 15 wherein the computer program further causes the computer to reconstruct a two-dimensional image for the sinogram, the two-dimensional image comprised of a plurality of voxels.

17. The computer readable storage medium of claim 16 wherein the computer program further causes the computer to:
determine the location of each of the plurality of voxels within a reconstruction cylinder; and
form an image on a rectilinear grid from the plurality of voxels based on interpolation of the plurality of voxels.

18. The computer readable storage medium of claim 15 wherein the computer program further causes the computer to calculate an inconsistency among the x-rays in the cone beam projection data and to perform an iterative gradient descent algorithm to minimize the inconsistency.

19. The computer readable storage medium of claim 18, wherein the computer program further causes the computer to store the minimized inconsistency among the x-rays in the cone beam projection data in a memory area to facilitate enhanced response time in a subsequent formation of the two-dimensional sinogram for the selected view angle.

20. The computer readable storage medium of claim 15 wherein the computer program further causes the computer to select a desired number of image surfaces to be determined from the identified measured x-rays.

21. The computer readable storage medium of claim 15 wherein the computer program further causes the computer to define each of the cone angle and the redundancy weight as functions of the view angle and the in-plane displacement from the rotation axis.

22. The computer readable storage medium of claim 15 wherein the computer program further causes the computer to select a free parameter for calculating an inconsistency between the identified measured x-rays, wherein the free parameter represents a weighted average of each of the identified measured x-rays and a conjugate of each of the identified measured x-rays.

23. A method of image reconstruction of cone beam computed tomography (CT) data comprising the steps of:
receiving x-ray projection data in a helix pattern for a plurality of points along a longitudinal axis;

for a selected view angle:
: identifying measured x-rays consistent with each other;
: generating a two-dimensional sinogram based on the identified measured x-rays; and
: defining a two-dimensional image surface based on the identified measured x-rays.

24. The method of claim 23 further comprising:
calculating an inconsistency among x-rays in the projection data; and
minimizing the inconsistency among the x-rays.

25. The method of claim 24 wherein the step of calculating the inconsistency further comprises selecting a variable parameter to estimate a line integral of an x-ray that passes through an intersection point of two x-rays in the projection data.

26. The method of claim 24, further comprising storing the minimized inconsistency among the x-rays in a memory area to facilitate enhanced response time in a subsequent formation of the two-dimensional sinogram for the selected view angle.

27. The method of claim 23 further comprising the step of reconstructing the two-dimensional sinogram at each of a plurality of view angles.

28. The method of claim 27 further comprising the step of axially interpolating the reconstructed two-dimensional sinograms to a rectilinear grid.

29. The method of claim 23 wherein the step of forming further comprises forming a two-dimensional sinogram having a view angle range of at least 180 degrees of the image surface.

* * * * *